(12) United States Patent  
Genereux et al.

(10) Patent No.: US 8,852,073 B2  
(45) Date of Patent: Oct. 7, 2014

(54) RELAXATION INDUCING SLEEP MASK

(75) Inventors: Philippe J. Genereux, Ottawa (CA); Troy G. Anderson, Marblehead, MA (US); Rudy A. Vandenbelt, Ottawa (CA)

(73) Assignee: Headwater R&D Inc, Ottawa (CA)

( * ) Notice: Subject to any disclaimer, the term of this patent is extended or adjusted under 35 U.S.C. 154(b) by 145 days.

(21) Appl. No.: 13/351,516

(22) Filed: Jan. 17, 2012

(65) Prior Publication Data

US 2013/0184516 A1 Jul. 18, 2013

(51) Int. Cl.
*A61M 21/02* (2006.01)

(52) U.S. Cl.
CPC .................................... *A61M 21/02* (2013.01)
USPC ............................................................ 600/25

(58) Field of Classification Search
USPC ...................................................... 600/26–28
See application file for complete search history.

(56) References Cited

U.S. PATENT DOCUMENTS

2009/0216070 A1* 8/2009 Hunt et al. .................. 600/27

* cited by examiner

*Primary Examiner* — Christine Matthews
*Assistant Examiner* — Joshua D Lannu
(74) *Attorney, Agent, or Firm* — Albert Peter Durigon (57) ABSTRACT

A relaxation inducing sleep mask includes a comfortable eye mask and a sleep module carried by the eye mask providing audible and/or visible patterns each intended to promote relaxation and to induce sleep.

11 Claims, 5 Drawing Sheets

RELAXATION INDUCING SLEEP MASK

FIELD OF THE INVENTION

This invention is drawn to the field of sleep or relaxation inducing therapy devices, and more particularly, to a novel relaxation inducing sleep mask.

BACKGROUND OF THE INVENTION

Sleep and hence relaxation techniques are vitally important in today's overstimulated and highly stressed world.

Eye masks with a light-tight design which provides a condition of total darkness are known to help stimulate melatonin production and thus serve to promote a state of sleep. The agitation of the prospective sleeper due to such factors as worries about job stress, disease, aging and children etc. is often enough to prevent the attainment of the sleep state notwithstanding use of such melatonin producing light-tight eye masks.

It is known art to provide an array of vertically spaced apart photoluminescent stripes of blue/green color in the eye cavities of a light-tight sleep mask that may be used as a template to direct and fix the eyes in such a way as to promote relaxation and induce sleep. The blue and green colors, however, have been shown by medical studies to reduce melatonin production and thus help prevent people from falling asleep, especially when the blue and green color is bright. What is needed are photoluminescent stripes of colors that do not have an intrinsic waking effect.

In use, the eyes of the wearer of such prior art sleep masks are directed in sequence from the lowest stripe upwardly through each next stripe and the gaze of the eyes is fixed on an uppermost one of the photoluminescent blue and green stripes. A meditative one-pointedness of mind, that is induced by fixing the gaze on an uppermost one of the photoluminescent blue/green stripes, counteracts any present mental agitation to induce the kind of equipoise that is conducive to sleep. Once charged, the photoluminescent stripes decay at their own rate and their lingering brightness may materially affect melatonin production. What is needed is a way to control the brightness and/or to eliminate any undesirable effects of lingering brightness.

The sequence of directing the eyes of the wearer of such prior art sleep masks from the lowermost stripes upwardly and of fixing the eyes on uppermost ones of the photoluminescent stripes of blue/green color is subject to distraction and to misdirection. What is needed is a way to guide the requisite upward sequencing and fixing motion from lower to uppermost stripes that allows anyone at any time to fix their gaze on an uppermost stripe in a manner that prevents distraction and misdirection.

The array of vertically spaced photoluminescent stripes of blue/green color of such prior art sleep masks serves as a template by means of which the requisite sequencing and fixation is performed. What is needed is an object that in its intrinsic presentation of itself tends to induce a meditative one-pointedness of mind that counteracts agitation to induce the kind of relaxation that is conducive to sleep but does not require any performative steps on behalf of the wearer in order to induce relaxation and sleep.

The one-pointedness of mind counteracting agitation of such prior art sleep masks that is induced by the wearer's intentionally directed eye motion upwardly along the array of photoluminescent stripes of blue/green color and fixation of the gaze upon uppermost ones of the array of photoluminescent elements of blue/green color may not work for everyone every time. What is needed are selectably alternative ways to counteract agitation to induce relaxation and sleep to make the benefits of relaxation available to more people more often.

SUMMARY OF THE INVENTION

A preferred embodiment of the invention has one or more the following features:

photoluminescent stripes of color having predominantly red-shifted components which have an intrinsic, biologically-calming effect;

stripes whose illumination is controllably extinguished at different user selectable dimming times and intensities to suit personal tastes and to eliminate lingering brightness so as not to disturb melatonin production;

photoluminescent objects that in their intrinsic presentation of themselves tend to induce a meditative one-pointedness of mind counteracting agitation that is conducive to sleep but does not require any performative steps on behalf of the wearer in order to induce relaxation and sleep;

stripes that are controllably illuminated in sequence to guide the eye upward and fix its gaze to relax the body and induce the mind to go sleep;

elements that are controllably illuminated to provide a visible pattern of such intensity, rhythm and duration as to cause brainwave entrainment leading to relaxation and sleep; and elements that are controllably actuated to provide an audible pattern of such intensity and rhythm as to induce relaxation and sleep.

These, and other aspects and objects of the present invention will be better appreciated and understood when considered in conjunction with the following description and the accompanying drawings. It will be understood, of course, that the following description of the preferred embodiments of the present invention is given by way of illustration and not of limitation. Many modifications and changes may be made within the scope of the present invention without departing from the spirit of the appended claims and the present invention includes all such modifications.

BRIEF DESCRIPTION OF THE DRAWINGS

A clear conception of the advantages and features constituting the present invention, and of the construction and operation of typical mechanisms provided with the present invention, will become more readily apparent by referring to the exemplary, and therefore non-limiting embodiments illustrated in the drawings accompanying and forming a part of the specification, wherein:

FIG. 1 respectively shows in the FIGS. 1A, 1B, and 1C thereof a back and to the side elevation, a front elevation and a back elevation of one embodiment of the relaxation inducing sleep mask in accord with the present invention;

FIG. 4 respectively shows in the FIGS. 4A, 4B, and 4C thereof a partially schematic front elevation, a partially schematic back elevation, and partially exploded, back and to the side elevation of another embodiment of the relaxation inducing sleep mask in accord with the present invention;

DETAILED DESCRIPTION THE PRESENTLY PREFERRED EMBODIMENTS

Figure 1A:
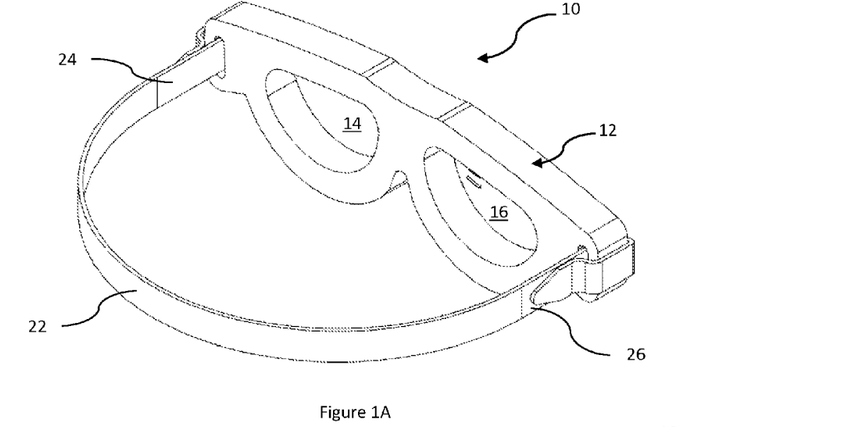
Figure 1B:
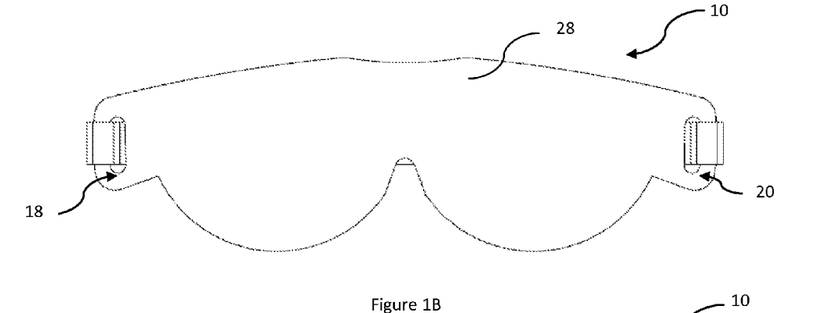
Figure 1C:
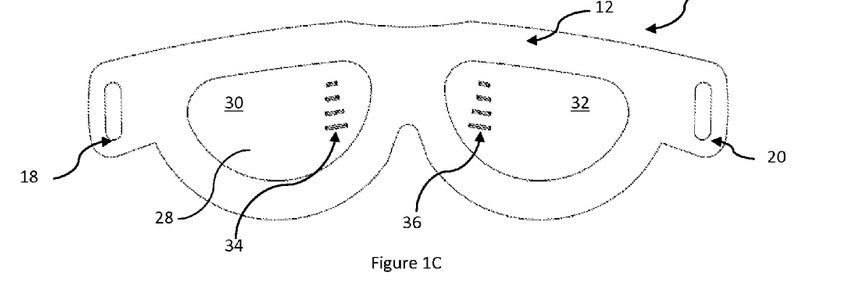

Referring now to FIG. 1, generally designated at 10 is one of the presently preferred embodiments of the relaxation and sleep inducing mask in accord with the present invention. The relaxation inducing sleep mask 10 includes a first body portion generally designated 12 of soft material such as foam that is of preselected height and width selected to bridge the forehead and upper lip between the temples to serve as an eye mask. Although a foam material is presently preferred, any material or lamination of materials soft and comfortable enough to sleep in may be employed.

The body portion 12 is provided with first walls defining laterally symmetrical left and right eye openings generally designated 14, 16 intermediate its sides and with second walls defining openings generally designated 18, 20 respectively proximate its lateral ends.

A strap 22 having free ends and separable fasteners 24, 26 at its free ends is attached to the body portion 12 such that each of its free ends is respectively threaded through another one of the openings 18, 20 and then folded back onto itself to releasably attach the strap 22 to the body 12 with an adjustable girth to comfortably fit an individual's head. Although a strap with Velcro™ ends laced through body openings provided therefor is presently preferred, any suitable means for providing a girth adjustable head strap that is comfortable enough to wear to sleep may be employed.

An opaque fabric 28 or other opaque compliant material is adhesively or otherwise joined to the front of the body 12. It will be readily appreciated that when the mask is seated on the face, the walls defining the openings 14, 16 and the included wall of the fabric 28 define light-tight eye cavities 30, 32.

A vertical array of photoluminescent stripes generally designated 34, 36 of color shifted to the red portion of the spectrum is imprinted on the inside surface of the cover 28 in each of the left and right eye cavities 30, 32. The light of the red-shifted photoluminescent stripes of the vertical arrays 34, 36 respectively visible in the left and right eye cavities 30, 32 is biologically calming and intrinsically does not have a waking or biologically stimulating effect. "Red-shifted" photoluminescent stripes is used herein to mean any material or pigment or combination of materials or pigments having predominantly more reds (and/or oranges) then blues (and/or greens). In the presently preferred embodiment, the vertical arrays of red-shifted photoluminescent stripes 34, 36 is fabricated by a silk-screen process. For each stripe of the arrays of stripes 34, 36, a white base layer is applied by silkscreening, and over that, three (3) passes of red-shifted photoluminescent pigment material are silkscreened. Of course, many other methods of and means for providing vertical arrays of red-shifted photoluminescent material in the left and right eye cavities will be evident to those of skill in the art without departing from the inventive concepts.

Figure 2:
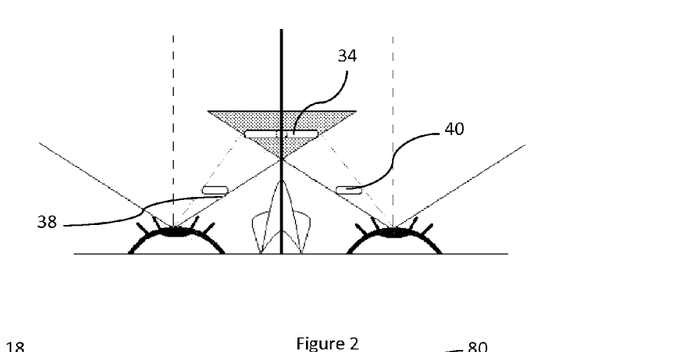
FIG. 2 is a ray trace diagram useful in explaining the manner that stereoscopic images are obtained.

The arrays 34, 36 of vertically spaced, red-shifted photoluminescent stripes present themselves as a single, stereoscopic image when viewed from within the eye cavities 30, 32 of the relaxation inducing sleep mask 10. To form a stereoscopic image as shown in FIG. 2, the arrays of vertically spaced, red-shifted photoluminescent stripes schematically illustrated at 38, 40 are forwardly spaced at a point somewhere in the optical near field of the eyes a distance large enough to prevent annoying interference with the eyelashes and are laterally located respectively such that there is at least a portion to the right of the left eye and to the left of the right eye. In the FIG. 1 embodiment, as best seen in FIG. 1C, this is accomplished by providing a wall depth of body 12 deep enough to provide the cavities 30, 32 with eyelash clearance at a depth where the cover 28 is within the optical near field, and by laterally symmetrically imprinting the vertically spaced arrays of red-shifted photoluminescent stripes 34, 36 on the inside of that portion of the cover 28 that is proximate to but spaced from the respective inside edges of the left and right eye cavities 34, 36.

In use, the vertical arrays 34, 36 of red-shifted photoluminescent stripes are charged by exposure to an external light source, not shown. Then, the mask 10 is put on the head and the free ends of the strap 22 are adjusted until comfortable. The wearer thereafter directs his eyes upwardly from the bottom stripe of the stereoscopic array successively to each next stripe and fixes his gaze on an uppermost one of the photoluminescent stripes of biologically calming reddish color. The gaze is held there. The fixation on an uppermost stripe, rhythmic breathing and the intrinsically biologically calming effects of the reddish color (or red-shifted color), synergistically cooperate to relax the body and induce the wearer to go to sleep. The red-shifted light of the photoluminescent stripes slowly fades until a condition of near total darkness prevails in the eye cavities 30, 32.

In accord with other embodiments of the present invention, different preferably red-shifted and stereoscopic photoluminescent images other than a vertically spaced apart array of red-shifted photoluminescent stripes are contemplated. In accord with these embodiments, the preferably red-shifted and stereoscopic photoluminescent image is selected to intrinsically represent a sensible pattern that in and of itself interacts with the wearer viewing the same to relax the body and induce the mind to restful sleep. For example, a "circle" pattern is a pattern which may advantageously be employed. As will be appreciated, it symbolizes something in the intrinsic representation of itself which, as closed and at rest in itself, may symbolically induce the kind of relaxation leading to sleep. Or the image employed may represent a pile of "spa rocks," or other symbol or icon intrinsically denoting or suggesting relaxation or sleep. Many agitation counteracting, relaxation and sleep inducing patterns may be selected without departing from the inventive concepts. Any such pattern may be silkscreened or otherwise provided on the inside face of the cover for stereoscopic viewing from within the left and right eye cavities without departing from the inventive concepts.

Figure 3A:
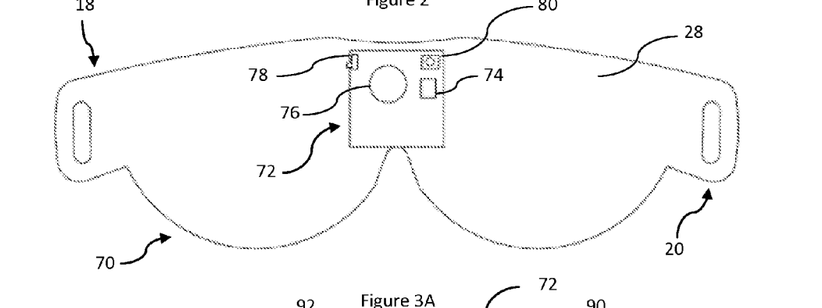
FIGS. 3A, 3B respectively show a partially schematic front elevation and a partially schematic back elevation of another embodiment of the relaxation inducing sleep mask in accord with the present invention.
Figure 3B:
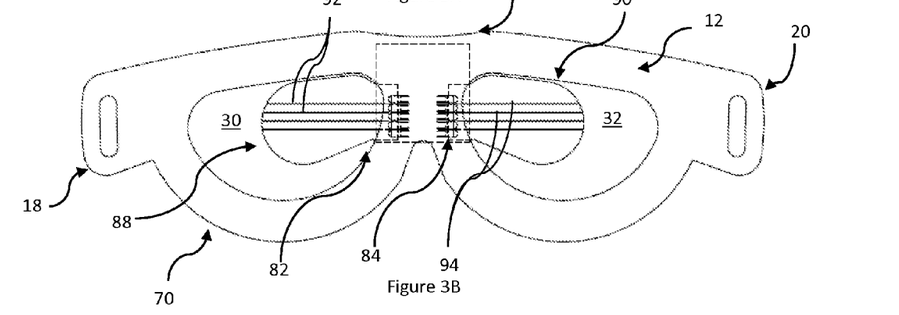

Referring now to FIGS. 3A, 3B, generally designated at 70 is another embodiment of the relaxation inducing sleep mask in accord with the present invention. The relaxation inducing sleep mask 70 includes foam body 12 and cover 28 configured, as described hereinabove, to provide left and right eye cavities 30, 32. A strap having ends and separable fasteners at its ends, not shown, is attached to the openings 18, 20.

A printed circuit board (PCB) generally designated 72 is mounted to the sleep mask 70. For example, the PCB may be mounted to the mask 70 by attaching it to the cover 28 by means of a two-part back plate and tray, not shown, that receive the PCB and hold it onto the cover 28. Many other means for and methods of mounting the PCB 72 to the mask 70 will become apparent to those of skill in the art without departing from the inventive concepts.

The printed circuit board 72 includes a processor implemented controller 74 including program and data memory and an ALU, not shown. Although the printed circuit board 72 is shown mounted to the bridge of the sleep mask, it could be carried in a different portion of the sleep mask, such as on the strap, or even be positioned away from the sleep mask itself, and coupled thereto in any manner known to those of skill in the art. As will be readily understood, although in the exemplary embodiments shown and described herein, the controller is mounted to the nose bridging portion of the sleep mask, it could be alternately coupled to the sleep mask in any suitable manner.

Figure 3C:
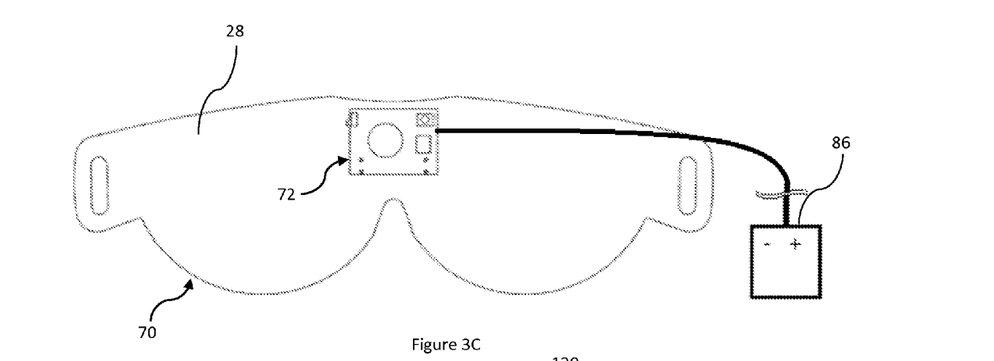
FIG. 3C shows a partially schematic, front elevation of the FIGS. 3A, 3B embodiment modified for use with an external power source.

The controller 74 is operatively coupled to a battery 76, an "on/off" switch 78, mode switch 80, and to left and right arrays generally designated 82, 84 of vertically spaced LEDs mounted to the PCB 72 or otherwise carried by the sleep mask laterally pointing respectively towards the left and right eye cavities 30, 32 of the body 12. As shown in FIG. 3C, an external battery 86, in lieu of or supplemental to the battery 76, may be operatively coupled to the controller 74 of the printed circuit board 72.

Optical diffusers generally designated 88, 90 are mounted to the mask 70 respectively in the left and right eye cavities 30, 32. For example, the optical diffusers 88, 90 may be held in openings provided therefor in a foam capture sleeve, not shown, which is attached to the mask between an apertured back layer, not shown, and the cover 28. Many other methods and means for mounting the optical diffusers to the mask will become apparent to those skilled in the art without departing from the inventive concepts.

The diffusers 88, 90 provide an array of alternating, vertically spaced opaque and optically transmissive portions 92, 94. The opaque portions 92 optically isolate the optically transmissive portions 94 from each other. Each of the optically transmissive portions 94 of the diffusers 88, 90 is laterally aligned with another one of the LEDs of the vertically spaced LED arrays 82, 84.

The diffusers 88, 90 are mounted preferably in stereoscopic position at the backs and at respective inside corners of the left and right eye cavities 30, 32. As will be readily appreciated, the optically transmissive portions 94 of the diffusers 88, 90 are each illuminated throughout its lateral length when its corresponding LED shines without exciting vertically adjacent portions 94 and appears as an image visible within the left and right cavities 30, 32 of the mask 70. Any suitable means, may, of course, be employed other than the LED arrays 82, 84 and cooperative diffusers 88, 90 to provide images individually visible within the left and right cavities 30, 32 of the mask 70 without departing from the inventive concepts.

In one user-selectable and preprogrammed mode, the controller 74 is operative to serially illuminate vertically coordinate pairs of the LEDs of the LED arrays 82, 84, starting from the bottommost pairs, upwardly illuminating each next LED pair alternately in sequence, with the sequence terminating in maintaining an uppermost pair of the LEDs lighted. The corresponding vertically coordinate pairs of stripes 94 are sequentially backlit thereby.

The eyes of the wearer naturally follow the sequence of images of the controllably moving luminous pattern produced within the left and right cavities 30, 32 of the mask 70, with the result that the eyes themselves are moved upwardly and fixed in an upward position, without the possibility of misdirection and the distraction occasioned thereby, inducing a one-pointed state of mind that counteracts agitation and is conducive to going to sleep.

The controller 74 may be programmed in different modes to repeat the sequential pattern a predetermined number of times, each with the same or a different rhythm and/or intensity and/or other parameter.

After a predetermined duration, determined to allow the typical user to have fallen asleep, the controller is operative to turn all the LEDs "off" in order to establish a condition of total darkness in the eye cavities. In different user selectable modes, different durations until total darkness may be provided and/or different intensities and/or different colors until total darkness could be employed. The different pre-programmed modes may be selected by mode switch 80.

As in other preferred embodiments described herein, the color of the controllably moving luminous pattern of images visible within the left and right cavities 30, 32 of the mask 70 may be selected to be red-shifted so as to predominate in color at and towards the red end of the color spectrum. As will be appreciated by those of skill in the art, this can be accomplished by any suitable means such as appropriate selection of the LEDs themselves, or other light sources, the use of filters, the use of a colored diffuser substrate material or additive and/or a combination thereof or other means.

Figure 4A:
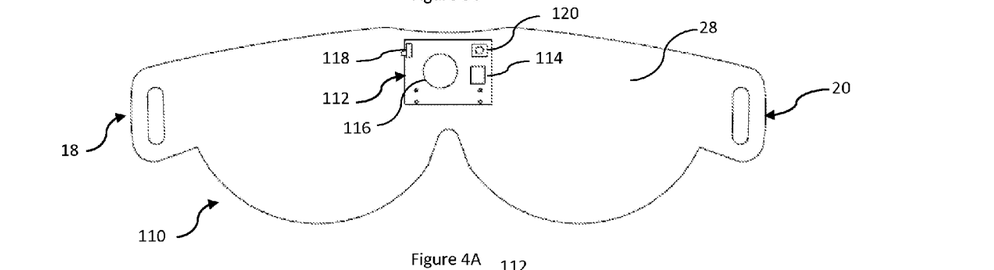
Figure 4B:
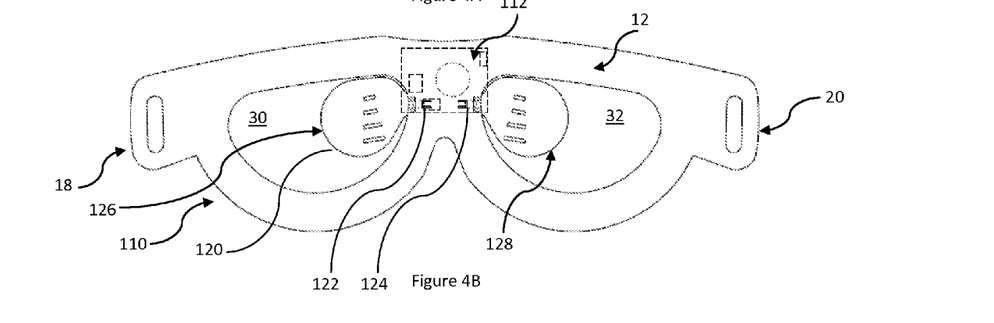
Figure 4C:
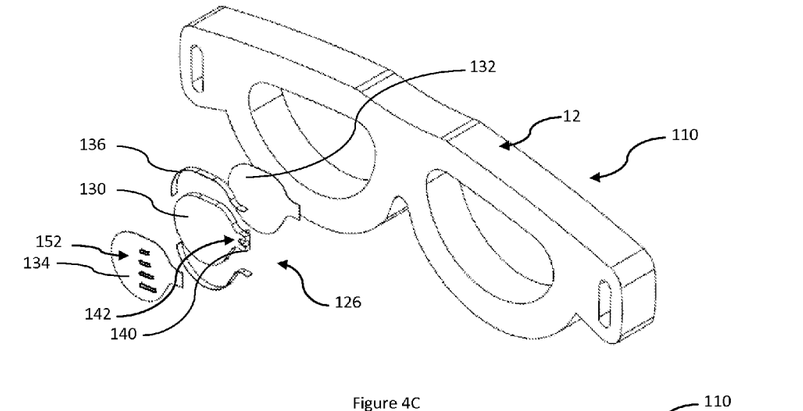

Referring now to FIGS. 4A, 4B, 4C, generally designated at 110 is another embodiment of a relaxation inducing sleep mask in accord with the present invention. The relaxation inducing sleep mask 110 includes foam body 12 and cover 28 configured, as above described, to provide left and right eye cavities 30, 32. A strap, having free ends and separable fasteners at its ends, not shown, is attached to the openings 18, 20.

A printed circuit board generally designated 112 is mounted to the sleep mask 110. For example, the PCB may be mounted to the mask 110 by attaching it to the cover 28 by means of a two-part back plate and tray, not shown, that receive the PCB and hold it onto the cover 28. Many other means for and methods of mounting the PCB 112 to the mask 110 will become apparent to those of skill in the art without departing from the inventive concepts. Although the printed circuit board 112 is shown mounted to the bridge of the sleep mask, it could be carried in a different portion of the sleep mask, such as on the strap, or even be positioned away from the sleep mask itself, and coupled thereto in any manner known to those of skill in the art.

The printed circuit board 112 includes a processor implemented controller 114 operatively coupled to battery 116, power "on/off" switch 118, mode switch 120 and left and right LEDs 122, 124 mounted to the PCB 112 or otherwise carried by the sleep mask laterally pointing respectively towards the left and right eye cavities 30, 32 of the body 12. An external power supply, not shown, could be provided.

Optical diffusers generally designated 126, 128 respectively provided in the left and right eye cavities 30, 32 preferably in stereoscopic position at the back of and towards the inside corners of the cavities are mounted to the sleep mask. For example, the optical diffusers 126, 128 may be held in openings provided therefor in a foam capture sleeve, not shown, which is attached to the mask between an apertured back layer, not shown, and the cover 28. Many other methods of and means for mounting the optical diffusers to the mask will become apparent to those skilled in the art without departing from the inventive concepts.

As shown in FIG. 4C, the diffusers 126, 128 each include an optically transmissive substrate 130 having proximate and distal surfaces and a peripheral edge. A reflective backing 132 is provided to its distal surface, an opaque cover 134 is provided to its proximate surface and a reflective border 136 is provided to its peripheral edge. The opaque cover 134 in the illustrated exemplary embodiment is etched to provide a pattern generally designated 152 of a vertically spaced line array. In the presently preferred embodiment, the reflective back and edge, and opaque cover, of the substrate 136 are coated on the corresponding surfaces of the substrate 136, although separate laminations applied adhesively or other means could be employed.

Figure 4D:
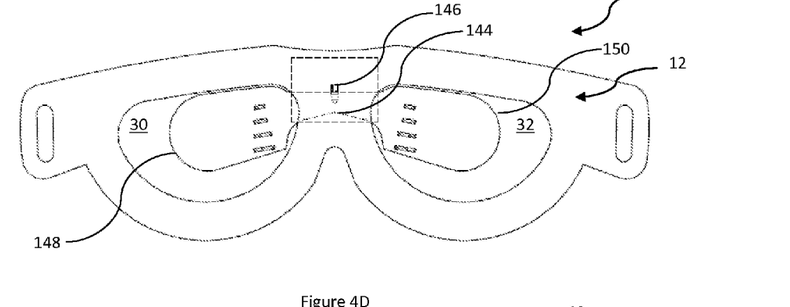
FIG. 4D shows a partially schematic back elevation of the FIGS. 4A-4C embodiment modified for use with a single LED.

The substrate 130 of the diffusers 126, 128 has a laterally extending flange 140, the end of which is shaped to provide an LED receiving seat generally designated 142. Referring now briefly to FIG. 4D, the flanges could be modified to accept the confronting ends of a beam splitter 144 mounted at the bridge of the eye mask and a single LED 146 could be employed to simultaneously backlight both diffusers 148, 150 via the beam splitter 144.

The LEDs 122, 124 are controllably actuated in accord with different modes described hereinbelow. Due to the reflective distal and peripheral surfaces and partially opaque proximate surface of the diffusers 126, 128, the light of the LED's 122, 124 in any mode is coupled through the seats 142 into the substrate 130 of the diffusers 126, 128, backlighting the pattern 152, thereby producing a stereoscopic image thereof that is visible in the left and right eye cavities 30, 32 of the relaxation inducing sleep mask 110. Any suitable pattern and any suitable diffuser backlighting that pattern could be employed without departing from the inventive concepts.

The FIG. 4 embodiments of the relaxation inducing sleep mask of the present invention provide selectable multi-mode operability, allowing for different relaxation techniques pre-programmed in the controller 114 thereof to be employed at will to match different sleep situations and users.

In one user-selectable and preprogrammed mode, the controller 114 is programmed to light the LEDs 122, 124 to render the stereoscopic image of the pattern 152 of the vertically spaced line array visible in the left and right eye cavities 30, 32. As in the embodiments described hereinabove, the user then directs his eyes using the stereoscopic pattern as a template sequentially upwardly from lowermost lines upwardly and fixes the gaze at an uppermost line in order to relax her body and to induce sleep. After a predetermined time, the controller turns the LEDs "off" and may be programmed to progressively dim the brightness of the LEDs before turning them "off" completely.

In another mode, the controller is programmed to illuminate the LEDs to thereby backlight the pattern 152 in a "pacing" relaxation mode. In this user-selectable mode, the controller is operative to illuminate the LEDs to backlight the pattern 152 initially at constant brightness and thereafter to pulse the LEDs to backlight the pattern with a predetermined rhythm, intensity and duration selected to entrain brainwaves to one or more Alpha relaxation and Delta and Theta sleep states or other brainwave states to induce relaxation and/or sleep. For example, "On-off" and/or "sinusoidal" pulsing may be employed.

Exemplary (well known) brainwave states and the associated frequencies/rhythms are Alpha wave entrainment (3-12 Hz), Relaxation; Theta entrainment (4-8 Hz), Lite Sleep; and Delta wave entrainment (0.5-4 Hz), Deep Sleep. The pacing can be achieved through embedding the frequencies in pulsations of the LED brightness either in both LEDs in sink or out of sync. The effect may be achieved by pulsing each LED independently at a frequency which differs by the desired entrainment frequency. For example, the right LED could be pulsing at five-hundred (500) Hz while the left LED pulses at five-hundred-ten (510) Hz. This would have the effect of a ten (10) Hz entrainment.

Figure 5:
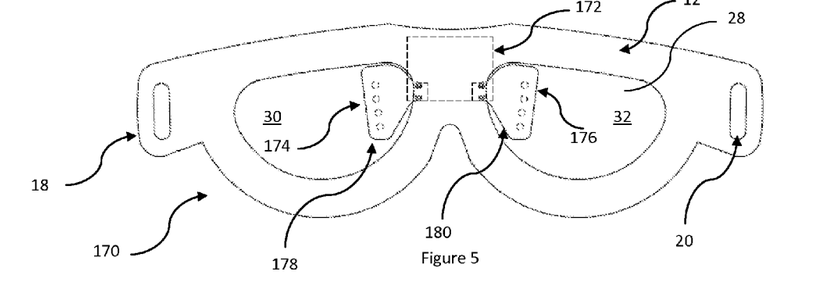
FIG. 5 shows a partially schematic back elevation of a further embodiment of the relaxation inducing sleep mask in accord with the present invention.

Referring now to FIG. 5, generally designated at 170 is another embodiment of the relaxation inducing sleep mask in accord with the present invention. As in the other embodiments described herein, the relaxation inducing sleep mask 170 includes foam body 12 and cover 28 configured, as described herein, to provide left and right eye cavities 30, 32. A strap, having free ends and separable fasteners at its ends, not shown, is attached to the openings 18, 20.

A printed circuit board generally designated 172 is mounted to the bridge of the sleep mask 172. For example, the PCB may be mounted to the mask 170 by attaching it to the cover 28 by means of a two-part back plate and tray, not shown, that receive the PCB and hold it onto the cover 28. Many other means for and methods of mounting the PCB 172 to the mask 170 will become apparent to those of skill in the art without departing from the inventive concepts. Although the printed circuit board 172 is shown mounted to the bridge of the sleep mask, it could be carried in a different portion of the sleep mask, such as on the strap, or even be positioned away from the sleep mask itself, and coupled thereto in any manner known to those of skill in the art. As will be readily understood, although in the exemplary embodiments shown and described herein, the controller is mounted to the bridge of the sleep mask, it could be alternately coupled to the sleep mask in any suitable manner.

The printed circuit board 172 includes a controller operatively coupled to a battery, a power "on/off" switch, and to a mode switch, each not shown, and to left and right vertically spaced arrays of LEDs generally designated 174, 176. LED array mounting members generally designated 178, 180 are respectively provided in stereoscopic position at the back and towards the inside corners the left and right eye cavities 30, 32 of the body 12 to receive the LEDs of the left and right vertically spaced arrays of LEDs 174, 176. For example, the array mounting members 178, 180 may be held in openings provided therefor in a foam capture sleeve, not shown, which is attached to the mask between an apertured back layer, not shown, and the cover 28. Many other methods and means for mounting the optical diffusers to the mask will become apparent to those skilled in the art without departing from the inventive concepts.

The LEDs of the arrays 174, 176 are mounted to the mounting members 178, 180 to face upwardly and outwardly of the left and right eye cavities 30, 32 of the body 12 to provide direct illumination of the eyes of the wearer. Any suitable means other than the LED arrays 174, 176 and cooperative mounting members 178, 180 may be employed to provide visible images within the left and right cavities 30, 32 of the mask 170 without departing from the inventive concepts.

An optical element, not shown, may be provided between the LEDs and the eyes. The element for example may be used to soften the light, or it for example may be provided with a visible pattern as described hereinabove, that, in it's intrinsic presentation of itself, tends to induce relaxation and/or sleep.

The FIG. 5 embodiments of the relaxation inducing sleep mask of the present invention provide selectable multi-mode operability, allowing for different relaxation techniques pre-programmed in the controller thereof to be employed at will to match different sleep situations and users.

In one user-selectable and preprogrammed mode, the controller is operative to light all of the LEDs of the vertically spaced arrays of LEDs 174, 176 at a constant intensity to provide a visible image of the vertically spaced LED arrays in the left and right eye cavities 30, 32. As in the embodiments described hereinabove, the user then directs his eyes, using the visible image as a template, sequentially upwardly from lowermost images upwardly and fixes the gaze at an uppermost image in order to relax his or her body to induce sleep. After a predetermined time, the controller turns all of the LEDs "off" and may be programmed to progressively dim the brightness of the LEDs before turning them "off" completely.

In a further user-selectable and preprogrammed mode, the controller is operative to sequentially light corresponding pairs of the LEDs of the left and right vertically spaced arrays of LEDs 174, 176 vertically upwardly, and to maintain uppermost pairs lighted, thereby directing the eyes to sequentially follow the stereoscopic image of the sequentially upwardly lighted pairs and directing the eyes to fix the gaze at the stereoscopic image of the uppermost lighted pair, therewith relaxing the body to induce sleep. After a predetermined time, the controller turns all of the LEDs "off" and may be programmed to progressively dim the brightness of the LEDs before turning them "off."

In another user-selectable and preprogrammed mode, the controller is programmed to illuminate the LEDs in a "pacing" relaxation mode. In this user-selectable mode, the controller is operative to illuminate the LEDs initially at constant brightness and thereafter to pulse the LEDs with a predetermined rhythm, intensity and duration selected to entrain brainwaves to one or more Alpha relaxation and Delta and Theta sleep states or other brainwave states to induce relaxation and/or sleep. The pacing can be achieved through embedding the frequencies in pulsations of the LED brightness either in both eye cavities in sink or out of sync. "On-off" and/or "sinusoidal pulsing may be employed. After a predetermined time, the controller turns all of the LEDs "off" and may be programmed to progressively dim the brightness of the LEDs before turning them "off," and/or to provide pulsing of the LEDs during the dimming phase.

In a further user-selectable and preprogrammed mode, the controller is programmed to provide a predetermined visible pattern of repeated dimming and brightening determined to simulate the "eye heaviness" feeling that precedes falling asleep. Repeated dimming and brightening of the LEDs over a short period of time simulates the feeling of nodding off, it feels like the user's eyes closing involuntarily. The predetermined visible pattern of repeated dimming and brightening determined to simulate the "eye heaviness" feeling that precedes falling asleep may, for example be thirty (30) cycles of fifteen (15) second dimming and brightening cycles for an exemplary fifteen (15) minute duration.

Figure 6A:
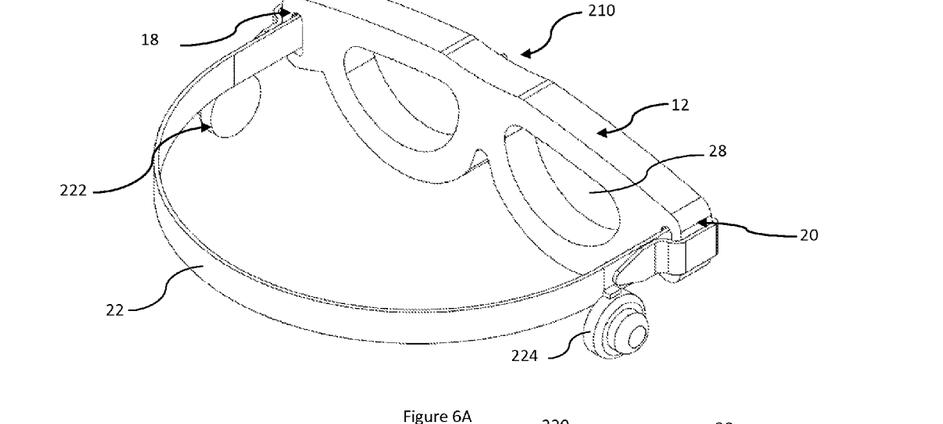
FIGS. 6A, 6B respectively show a partially schematic back elevation and partially schematic front elevation of a further embodiment of the relaxation inducing sleep mask in accord with the present invention.
Figure 6B:
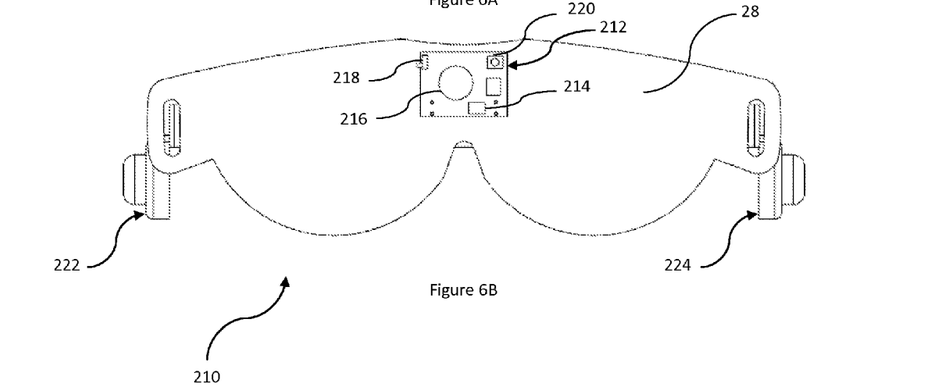

Referring now to FIG. 6, generally designated at 210 is another embodiment of a relaxation inducing sleep mask in accord with the present invention. The relaxation inducing sleep mask 210 includes foam body 12 and cover 28 configured, as above described, to provide left and right eye cavities 30, 32. An adjustable strap 22 is attached to the openings 18, 20.

A printed circuit board generally designated 212 is mounted to the bridge of the sleep mask 210. Although the printed circuit board 212 is shown mounted to the bridge of the sleep mask, it could be carried in a different portion of the sleep mask, such as on the strap, or even be positioned away from the sleep mask itself, and coupled thereto in any manner known to those of skill in the art. As will be readily understood, although in the exemplary embodiments shown and described herein, the controller is mounted to the bridge of the sleep mask, it could be alternately coupled to the sleep mask in any suitable manner.

The printed circuit board 212 includes a sound controller 214 operatively coupled to battery 216, power "on/off" switch 218, mode switch 220, and to left and right earphones respectively generally designated 222, 224 carried by strap 22. Preferably, the controller 214 includes program and data memory and an ALU, not shown, selectably operative to controllably produce sounds. An external power supply, not shown, could be provided. Any suitable commercially available or custom-designed sound controller could be employed without departing from the inventive concepts.

The controller 214 is operative to play sounds though the speakers 222, 224 to thereby relax the body and induce the mind to go to sleep. An external sound player, not shown, could also be employed. Any sounds such as nature sounds or calming and soothing music, or verbal cues, or tinittus relieving or other sounds in a predetermined audible pattern determined to counteract agitation and induce relaxation and sleep could be employed without departing from the inventive concepts.

As will be readily appreciated, the sound therapy provided by the FIG. 6 embodiments of the relaxation inducing sleep mask may be used alone and/or together with any of the hereinabove described embodiments without departing from the inventive concepts.

As will be readily appreciated, features of some embodiment may be combined with the features of other embodiments without departing from the inventive concepts. Although LEDs have been shown illustratively herein, other sources of illumination such as electroluminescent strips could be employed or other means known to those skilled in the art.

Among other exemplary modifications, the color need not be constant for any visible pattern but could change, and the color change feature can be provided as a user-selectable modal option, or provided as part of a preprogrammed mode.

The audible pattern and visible pattern could be related in synchronistic and symbiotic ways to synergistically promote relaxation and/or induce sleep. For example, synchronized or otherwise coordinated audible and visible pacing could be selected in a pre-programmed pacing mode.

Different sound reproduction other than earphones, such as a pillow or any other standalone speaker, could be employed.

Many other modifications and other embodiments of the claimed invention will become apparent to one of skill in the art having benefited from the instant disclosure.

What is claimed is:

1. A relaxation inducing sleep mask, comprising:
an eye mask adapted to be worn about the head of a user having a first portion configured to provide light-tight eye cavities confronting the left and right eyes of the user and a second portion configured to laterally extend from the first portion across the left and right ears around the head of the user;
a processor implemented controller and electro-optical means connected to said processor implemented controller coupled to the eye mask for providing a visible pattern of vertically spaced apart images simultaneously visible inside said eye cavities of said mask confronting the left and right eyes of the user that is of duration and intensity to allow the user to direct said left and right eyes in a successive upward, vertical direction from lowermost simultaneously visible images to uppermost simultaneously visible images and to fix said user's gaze on said uppermost visible images in order to relax the user and induce sleep in the user and thereafter said pattern of vertically spaced images simultaneously visible inside said eye cavities of said mask confronting the left and right eyes of the user is controllably extinguished;

wherein said electro-optical means includes a source of light controllably actuated by said processor implemented controller;
wherein said source of light includes first and second arrays of vertically spaced LEDs respectively mounted inside said eye cavities of said mask confronting the left and right eyes such that the LEDs of the first and second arrays of vertically spaced LEDs each have longitudinal axes that are generally parallel with longitudinal axes of said eye cavities of said mask so as to direct light from said LEDs rearwardly outwardly therefrom.

2. A relaxation inducing sleep mask, comprising:
an eye mask adapted to be worn about the head of a user having a first portion configured to provide light-tight eye cavities confronting the left and right eyes of the user and a second portion configured to laterally extend from the first portion across the left and right ears around the head of the user;
a processor implemented controller and electro-optical means connected to said processor implemented controller coupled to the eye mask for providing a visible pattern of vertically spaced apart images simultaneously visible inside said eye cavities of said mask confronting the left and right eyes of the user that is of duration and intensity to allow the user to direct said left and right eyes in a successive upward, vertical direction from lowermost simultaneously visible images to uppermost simultaneously visible images and to fix said user's gaze on said uppermost visible images in order to relax the user and induce sleep in the user and thereafter said pattern of vertically spaced images simultaneously visible inside said eye cavities of said mask confronting the left and right eyes of the user is controllably extinguished;
wherein said electro-optical means includes a source of light controllably actuated by said processor implemented controller;
wherein said electro-optical means further includes first and second optical means respectively mounted inside said eye cavities of said mask confronting the left and right eyes of the user that are optically coupled to said source of light.

3. The relaxation inducing sleep mask of claim 2, wherein said first and second optical means are patterned optical diffusers.

4. The relaxation inducing sleep mask of claim 2, wherein said source of light controllably actuated by said processor implemented controller includes first and second arrays of vertically spaced LEDs and wherein said first and second optical means include striated diffusers having vertically spaced optically transmissive portions that respectively receive the light beams of corresponding ones of the vertically spaced LEDs of the first and second arrays of vertically spaced LEDs.

5. A relaxation inducing sleep mask, comprising:
an eye mask adapted to be worn about the head of a user having a first portion configured to provide light-tight eye cavities confronting the left and right eyes of the user and a second portion configured to laterally extend from the first portion across the left and right ears around the head of the user;
a processor implemented controller and electro-optical means including a source of light controllably actuated by said processor implemented controller coupled to the eye mask for providing a pacing pattern of images visible inside said eye cavities of said mask confronting the left and right eyes of the user of predetermined rhythm, intensity, and duration determined to entrain preselected Alpha, Beta and Theta brainwave states in the user beholding the pacing pattern of images visible inside said eye cavities of said mask confronting the left and right eyes of the user in order to relax the user and induce sleep in the user and thereafter said pacing pattern of images visible inside said eye cavities of said mask confronting the left and right eyes of the user is controllably extinguished;
wherein said source of light includes first and second arrays of vertically spaced LEDs having at least one LED respectively mounted inside said eye cavities of said mask confronting the left and right eyes of the user such that the LEDs of the first and second arrays of at least one vertically spaced LEDs each have longitudinal axes that are generally parallel with longitudinal axes of said eye cavities of said mask so as to direct light from said LED arrays rearwardly outwardly therefrom.

6. A relaxation inducing sleep mask, comprising:
an eye mask adapted to be worn about the head of a user having a first portion configured to provide light-tight eye cavities confronting the left and right eyes of the user and a second portion configured to laterally extend from the first portion across the left and right ears around the head of the user;
a processor implemented controller and electro-optical means including a source of light controllably actuated by said processor implemented controller coupled to the eye mask for providing a pacing pattern of images visible inside said eye cavities of said mask confronting the left and right eyes of the user of predetermined rhythm, intensity, and duration determined to entrain preselected Alpha, Beta and Theta brainwave states in the user beholding the pacing pattern of images visible inside said eye cavities of said mask confronting the left and right eyes of the user in order to relax the user and induce sleep in the user and thereafter said pacing pattern of images visible inside the eye cavities confronting the left and right eyes is controllably extinguished;
wherein said electro-optical means further includes first and second optical means mounted respectively inside said eye cavities of said mask confronting the left and right eyes of the user that are optically coupled to said source of light.

7. The relaxation inducing sleep mask of claim 6, wherein said first and second optical means are patterned optical diffusers.

8. A relaxation inducing sleep mask, comprising:
an eye mask adapted to be worn about the head of a user having a first portion configured to provide light-tight eye cavities confronting the left and right eyes of the user and a second portion configured to laterally extend from the first portion across the left and right ears around the head of the user;
a processor implemented controller and electro-optical means including a source of light controllably actuated by said processor implemented controller coupled to the eye mask for providing an upwardly moving pattern of sequentially visible vertically spaced apart images sequentially moving inside said eye cavities of said mask confronting the left and right eyes of the user from lowermost to uppermost vertically spaced apart images that is of predetermined duration, rhythm and intensity determined to direct the eyes of the user to follow the upwardly moving pattern of sequentially visible vertically spaced images sequentially moving inside said eye cavities of said mask confronting the left and right eyes of the user from the lowermost to the uppermost vertically spaced images and to fix said user's gaze on the uppermost vertically spaced images in order to relax the user and induce sleep in the user and thereafter said upwardly moving pattern of sequentially visible vertically spaced images upwardly moving inside said eye cavities of said mask confronting the left and right eyes of the user from the lowermost to the uppermost vertically spaced images is controllably extinguished;

wherein said source of light includes first and second arrays of vertically spaced LEDs respectively mounted inside said eye cavities of said mask confronting the left and right eyes of the user such that the LEDs of the first and second arrays of vertically spaced LEDs each have longitudinal axes that are generally parallel with longitudinal axes of said eye cavities of said mask so as to direct light from said LEDs rearwardly outwardly therefrom.

9. A relaxation inducing sleep mask, comprising:

an eye mask adapted to be worn about the head of a user having a first portion configured to provide light-tight eye cavities confronting the left and right eyes of the user and a second portion configured to laterally extend from the first portion across the left and right ears around the head of the user;

a processor implemented controller and electro-optical means including a source of light controllably actuated by said processor implemented controller coupled to the eye mask for providing an upwardly moving pattern of sequentially visible vertically spaced apart images sequentially moving inside said eye cavities of said mask confronting the left and right eyes of the user from lowermost to uppermost vertically spaced apart images that is of predetermined duration, rhythm, and intensity determined to direct the eyes of the user to follow the upwardly moving pattern of sequentially visible vertically spaced images sequentially moving inside said eye cavities of said mask confronting the left and right eyes of the user from the lowermost to the uppermost vertically spaced images and to fix the user's gaze on the uppermost vertically spaced images in order to relax the user and induce sleep in the user and thereafter said upwardly moving pattern of sequentially visible vertically spaced images upwardly moving inside said eye cavities of said mask confronting the left and right eyes of the user from the lowermost to the uppermost vertically spaced images is controllably extinguished;

wherein said electro-optical means further includes first and second optical means mounted respectively inside said eye cavities of said mask confronting the left and right eyes of the user that are optically coupled to said source of light.

10. The relaxation inducing sleep mask of claim 9, wherein said source of light controllably actuated by said processor implemented controller includes first and second arrays of vertically spaced LEDs and wherein said first and second optical means include striated diffusers having vertically spaced optically transmissive portions that respectively receive the light beams of corresponding ones of the vertically spaced LEDs of the first and second arrays of vertically spaced LEDs.

11. A relaxation inducing sleep mask, comprising:

an eye mask adapted to be worn about the head of a user having a first portion configured to provide light-tight eye cavities confronting the left and right eyes of the user and a second portion configured to laterally extend from the first portion across the left and right ears around the head of the user;

a vertically spaced array of red-shifted photoluminescent stripes provided in each said left and right eye cavities of said mask;

wherein said vertical array of red-shifted photoluminescent stripes are provided in each of the cavities confronting the left and right eyes that results in a viewable single stereoscopic image.

* * * * *